US005750101A

United States Patent [19]

Stone

[11] Patent Number: 5,750,101
[45] Date of Patent: May 12, 1998

[54] OVO IMMUNIZATION OF AVIAN EMBRYOS WITH OIL-EMULSION VACCINES

[75] Inventor: Henry D. Stone, Winterville, Ga.

[73] Assignee: The United States of America, as represented by the Secretary of Agriculture, Washington, D.C.

[21] Appl. No.: 530,698

[22] Filed: Sep. 15, 1995

Related U.S. Application Data

[63] Continuation-in-part of Ser. No. 269,325, Jun. 30, 1994, abandoned.

[51] Int. Cl.$^6$ .............. C12N 5/00; C12N 15/00; A61K 48/00
[52] U.S. Cl. .............. 424/85.2; 530/350; 530/351; 514/2; 514/44; 424/93.1; 424/93.21
[58] Field of Search ............... 424/85.2, 209.1, 424/93.1, 93.21; 119/6.8, 6.9

[56] References Cited

U.S. PATENT DOCUMENTS

| | | | |
|---|---|---|---|
| 2,851,006 | 9/1958 | Taylor et al. | 119/6.8 |
| 4,040,388 | 8/1977 | Miller | 119/6.8 |
| 4,458,630 | 7/1984 | Sharma et al. | 119/1 |
| 5,106,617 | 4/1992 | Federicksen et al. | 424/85.2 |
| 5,176,101 | 1/1993 | Paul et al. | 119/6.8 |
| 5,206,015 | 4/1993 | Cox et al. | 424/93 |

OTHER PUBLICATIONS

Brugh et al., Am. J. Vet. Res., 40, 1979, 165–169.
Stone et al., Avian Diseases, 22(4), Received 15 May 1978, 666–674.
Avian Diseases 34:979–983, 1990. Stone et al. Efficacy of Experimental Newcastle Disease Water-in-Oil Emulsion Vaccines Formulated from Squalane and Squalene.
Avian Diseases 37:000–000, 1993. Gast et al. Evaluation of the Efficacy of Oil-Emulsion Bacterins for Reducing Fecal Shedding of *Salmonella enteritidis* by Laying Hens.
Proc. 77th Annual Meeting U.S. Animal Health Assoc. St. Louis, Missouri. 1973. pp. 596–600. Beard et al.
Nonionic Surfactants. Marcel Dekker, Inc., New York. 1966. pp. 609–611.
Avian Diseases 27:688–697, 1983. Stone et al. Influence of Formulation on the Efficacy of Experimental Oil-Emulsion Newcastle Disease Vaccines.
Avian Diseases 34:721–728, 1990. Gast et al. Serological Detection of Experimental *Salmonella enteritidis* Infections in Laying Hens.
Avian Diseases 37:1085–1091, 1993. Gast et al. Evaluation of the Efficacy of Oil-Emulsion Bacterins for Reducing Fecal Shedding of *Salmonella enteritidis* by Laying Hens.
Avian Diseases 22(4):666–674. Received 15 May 1978. Stone et al. Preparation of Inactivated Oil-Emulsions Vaccines with Avian Viral or Mycoplasma Antigens.
Avian Diseases 37:399–405, 1993. Stone, Henry D. Efficacy of Experimental Animal and Vegetable Oil-Emulsion Vaccines for Newcastle Disease and Avian Influenza.

*Primary Examiner*—Suzanne E. Ziska
*Assistant Examiner*—Andrew Milne
*Attorney, Agent, or Firm*—Gail E. Poulos; M. Howard Silverstein; John Fado

[57] ABSTRACT

Avian diseases, particularly those which threaten birds early in life, are controlled by embryonal vaccination using oil emulsion vaccines. The site of inoculation is the albumin end of the egg via entry through the air cell end of the egg.

16 Claims, 6 Drawing Sheets

OVO IMMUNIZATION OF AVIAN EMBRYOS WITH OIL-EMULSION VACCINES

This is a continuation-in-part of application Ser. No. 08/269,325, filed Jun. 30, 1994, now abandoned, herein incorporated by reference.

BACKGROUND OF THE INVENTION

1. Field of the Invention

This invention relates to a method for immunizing avian embryos with oil-emulsion vaccines in ovo.

2. Description of the Prior Art

Manual administration of emulsion vaccines to young avian flocks requires handling of individual birds and may involve corporate liability claims when self-injection occurs accidentally. Newly hatched chicks have been routinely inoculated against disease prior to being placed in brooder houses. However, vaccines do fail because the young chicks may become exposed to a virulent form of a disease before vaccination or before they have developed adequate immunity from the vaccination.

There have been a number of reports of in ovo vaccination of avian embryos. In U.S. Pat. No. 5,206,015 ('015), to Cox et al., a method is disclosed for introducing an aqueous preparation of unattenuated probiotic bacteria into the digestive tract of a bird to exclude undesirable bacteria from colonizing the digestive tract. The bacterial culture is administered by depositing it in the air cell (large end) of an egg. The digestive tract of the hatchling of the innoculated eggs is found to be colonized by the bacterial culture at the time of hatch. In this method a hole is punched into the air cell end (large end) of the egg with a first sterile needle, then the bacteria is administered using a smaller sterile needle, and finally the hole is either left unsealed or sealed with a bacteria-impermeable material.

U.S. Pat. No. 4,458,630 ('630), to Sharma et al. discloses an embryonal vaccination for Marek's disease using unattenuated turkey herpesvirus (HVT) where the injection site is within either regions defined by the amnion or yolk sac. That is, the injection is midway along, and perpendicular to, the longitudinal axis for amnion penetration through the large end of the egg with a one inch needle so that the needle passes through the outer and inner shell membranes enclosing the air cell and amnion and terminates in the fluid above the chick or in the chick itself. As in '015 patent, a hole is punched or drilled in the shell and this may be resealed with paraffin or the like.

U.S. Pat. No. 4,040,388 ('388), to Miller teaches an automated method and apparatus for injecting embryonated eggs prior to incubation with a variety of substances into the albumin end (small end) of the egg. The reference teaches coagulative cooking of the surrounding albumin to seal the hole made by the injection. The drawbacks are that the vaccine is susceptible to inactivation during the heat coagulation step. Furthermore, Sharma et al. ('630) report that albumin has an inhibitory effect on the transport of an inoculant to the embryo at the egg's opposite end.

U.S. Pat. No. 2,851,006 ('006) to Taylor et al. teaches a method for increasing the hatch rate of bacterially infected eggs by means of in ovo treatment with a suitable bacteriophage in an aqueous preparation. The phage is introduced to the interior of the egg prior to incubation by any variety of techniques including by hypodermic syringe, pressure differential in a dipping fluid and jet spray. With the hypodermic syringe, a 26 gauge short shank needle is inserted at an oblique angle into the albumin end of the egg. The patent teaches that the hole is sealed with a cellulose tape patch or a drop of melted paraffin.

In U.S. Pat. No. 3,120,834 ('834), Goldhaft et al. expands the application taught in Taylor to a variety of substances including antibiotics, sulfonamides, vitamins, enzymes, nutrients, and inorganic salts. These agents are introduced through the shell prior to incubation by means of vacuum impregnation.

U.S. Pat. No. 3,256,856 ('856) to Nicely et al. offers an improvement to the method of Goldhaft et al. in providing one or more holes in the egg shell for facilitating penetration. The hole(s) is (are) made in the air cell end (large end) of the egg, not extending beyond the inner shell membrane. The commercial practicality of the vacuum impregnation technique is limited by the unreliability of obtaining a uniform treatment and the economic unfeasibility of charging the dipping vats with expensive vaccine.

Oil-emulsion vaccines prepared with mineral oil are highly efficacious formulations used widely against poultry diseases in various monovalent and polyvalent forms. Mineral oil vaccines cause excessive tissue reactogenicity, the oil persists too long, is practically non-digestible, and is considered carcinogenic. A 42 day holding period is required before slaughter of poultry if a mineral oil vaccine is administered. Animal and vegetable oil vaccines have been developed to replace mineral oil vaccines. However, these have also resulted in tissue reactions (Stone, Avian Diseases Vol. 34:979–983, 1990; Stone, Avian Diseases Vol. 37(2):399–405, 1993, all herein incorporated by reference).

While there are various methods for in ovo immunization using aqueous live vaccines and biologicals, there remains a need in the art for a method of in ovo immunization using oil-containing vaccines. The present invention provides a method which is different from prior art methods and overcomes problems associated with oil-containing vaccines and prior art in ovo immunization methods such as tissue reactogenicity and sealing the hole made to administer the vaccine to the embryo. Furthermore, inactivated antigens are successfully used in an in ovo oil emulsion vaccine.

SUMMARY OF THE INVENTION

It is therefore an object of the present invention to provide a method of in ovo immunization of avian embryos.

Another object of the present invention is to provide a method of in ovo immunization using oil emulsion vaccines.

A further object of the present invention is to provide a method of in ovo immunization of avian embryos wherein the post-hatch seroconversion is at least about 70%.

A still further object of the present invention is to provide a method of in ovo immunization of avian embryos wherein the post-hatch seroconversion is at least about 90%.

Another object of the present invention is to provide a method of in ovo immunization of avian embryos with a multivalent vaccine wherein the post-hatch seroconversion is at least about 65%.

A further object of the present invention is to provide a method of in ovo immunization of avian embryos wherein the needle gauge is from 27 to 16.

Another object of the present invention is to provide a method of in ovo immunization of avian embryos wherein the amount of vaccine deposited in the egg is from about 25 microliters to about 1.0 milliters.

A further object of the present invention is to provide a method of in ovo immunization wherein the vaccine is deposited near or into the albumin of the egg.

A still further object of the present invention is to provide an avian egg which includes an embryo which is immunized with an oil-emulsion vaccine.

Further objects and advantages of the invention will become apparent from the following description.

BRIEF DESCRIPTION OF THE DRAWINGS

FIG. 2 shows the embryo development from 9–10 days to 18 days of age. FIGS. 2A–2C are viewed from the large end. FIGS. 2D and 2E are viewed as the egg lays on its side. The embryo at day 18 is curled around the center line which allows needle 8 to usually miss the embryo during the injection process.

DETAILED DESCRIPTION OF THE INVENTION

The method of this invention is applicable to any avian animal, whether domestic or wild, and particularly to those which are commercially reared for meat or egg production. Without limitation thereto, exemplary avians include chickens, turkeys, geese, ducks, pheasants, and the like. Birds which are reared in high density brooder houses such as broiler and layer chickens are especially vulnerable to environmental exposure to infectious agents and would largely benefit from prehatch vaccination.

The advantages of this invention are in the prevention of lethal diseases which threaten avians early in life. Avian diseases include any disease or contamination of viral, bacterial, or other microbial origin. Examples of such, without limitation thereto, include Newcastle's disease, avian leukosis, infectious bursal disease, adenovirus disease, reovirus, pox, laryngotracheitis, infectious bronchitis, reticuloendotheliosis, influenza, infectious coryza, fowl typhoid, fowl cholera, Salmonella, and Marek's disease.

The prior art in ovo injection systems has shown that chickens are immune competent as late stage embryos and that the advantages of early immunization of convenience, safety, labor, and time-saving are evident. These advantages are also greatly desired for oil emulsion vaccine administration which requires even more time, labor, liability risks, and contact with chickens.

The term vaccine is defined to mean all types of biological agents used to produce active immunity or competitive exclusion.

Oil emulsion vaccines include any water-in-oil emulsion or oil-in-water emulsion which is compatible with avian tissues (Gast et al., Avian Diseases Vol 37(4), 1993; Stone, Avian Diseases Vol. 37:399–405, 1993; Stone et al., Avian Diseases, Vol. 34:979–983, 1990; Stone et al., Avian Diseases, Vol. 27(3):688–697, 1983; and U.S. Pat. No. 3,919,411, Glass et al., 1975, all herein incorporated by reference).

Examples of useful oils include mineral oil, such as Drakeol 6VR; terpene oils such as squalene and squalane; vegetable oils such as soybean oil, olive oil, corn oil, jojoba oil, peanut oil, cotton-seed oil, sunflower oil, safflower oil, sesame oil, apricot oil, avocado oil, wheat germ oil, canola oil, Linseed oil, and almond oil; fish oils such as shark oil, orange roughy oil, Menhaden oil, and cod liver oil; animal oils such as mink oil, lard oil, and chicken fat oil.

Examples of surfactants used in emulsion vaccines include Arlacel 80 (sorbitan monooleate), Tween 80 (Polysorbate 80), Span 80, Arlacel 83 (sorbitan sesquioleate), Arlacel 85 (sorbitan sesquioleate), and Tween 61 (polyoxyethylene sorbitan), for example. Surfactants suitable for animal and vegetable water-in-oil vaccines include crude yellow, and purified beeswax, for example. Furthermore, surfactants suitable for vaccines containing squalene and squalane include Arlacel and Tween 80.

Metabolizable oil emulsion vaccines are also useful in the present invention and are prepared as described in U.S. patent application Ser. No. 08/384,184 which is herein incorporated by reference (Stone).

It has been found that vaccinating and immunizing chick embryos with oil emulsion vaccines containing inactivated antigens in ovo induces protection in very young chicks through and beyond the life span of broiler chickens (>7 weeks). The vaccine is deposited on or near the inside surface of the small end 4 (albumin end) of egg 10 with needle 8 placed through the midline of the egg beginning at the large end 1 (air cell end) (see FIG. 1). Embryo 6 is curled around the center line which allows needle 8 to miss the embryo 6 proper when needle 8 follows the center line (see FIG. 2). Not all of the oil emulsion vaccine remains in the albumin 4. Since it is oil and lighter than the aqueous egg fluids, it floats upward when egg 10 is air-cell-up 1 (large end up) which is how the egg is placed for vaccination and further incubation prior to being placed on their sides in hatching trays. The vaccine becomes dispersed in the fluids of the egg by the movement of the embryo and the presence of the mixture of the surfactants which allows dispersement in aqueous medium by virtue of the surfactant hydrophilic groups. The phenomenon can be observed directly as the shell can be broken into small pieces and peeled off the chorion (the membrane next to the inner shell membrane) which encloses and keeps the entire embryo and membranes intact. The vaccine appears as milky white droplets. Furthermore, the vaccine is seen in many 1-day hatched chicks in the abdominal areas either subcutaneous (SC), intraperitoneal (IP) or in the wall of the peritoneal cavity. Before the embryo hatches, the skin completes its growth on the abdominal surface and in the process encloses the vaccine which sometimes can be seen subcutaneously in opened hatched chicks. This method simulates subcutaneous vaccination. Also as albumin 4 and yolk sac 5 enter the peritoneal cavity some of the vaccine may be enclosed intraperitoneally simulating intraperitoneal vaccination. Manual administration of emulsion vaccines to young chickens requires handling of individual chickens and may involve corporate liability when self-injection occurs accidentally.

Immunologic competence in avian embryos develops in the final quarter of the incubation period, before which embryos are highly susceptible to infectious agents. Therefore, avian embryos should be inoculated at least about three days prior to hatch. In the chicken, for example, an injection could be given between 15 and 18 days of incubation with a most preferable time being the eighteenth day of the 21 day incubation, corresponding to the time when embryonated eggs are routinely transferred to hatching trays.

Figure 1:
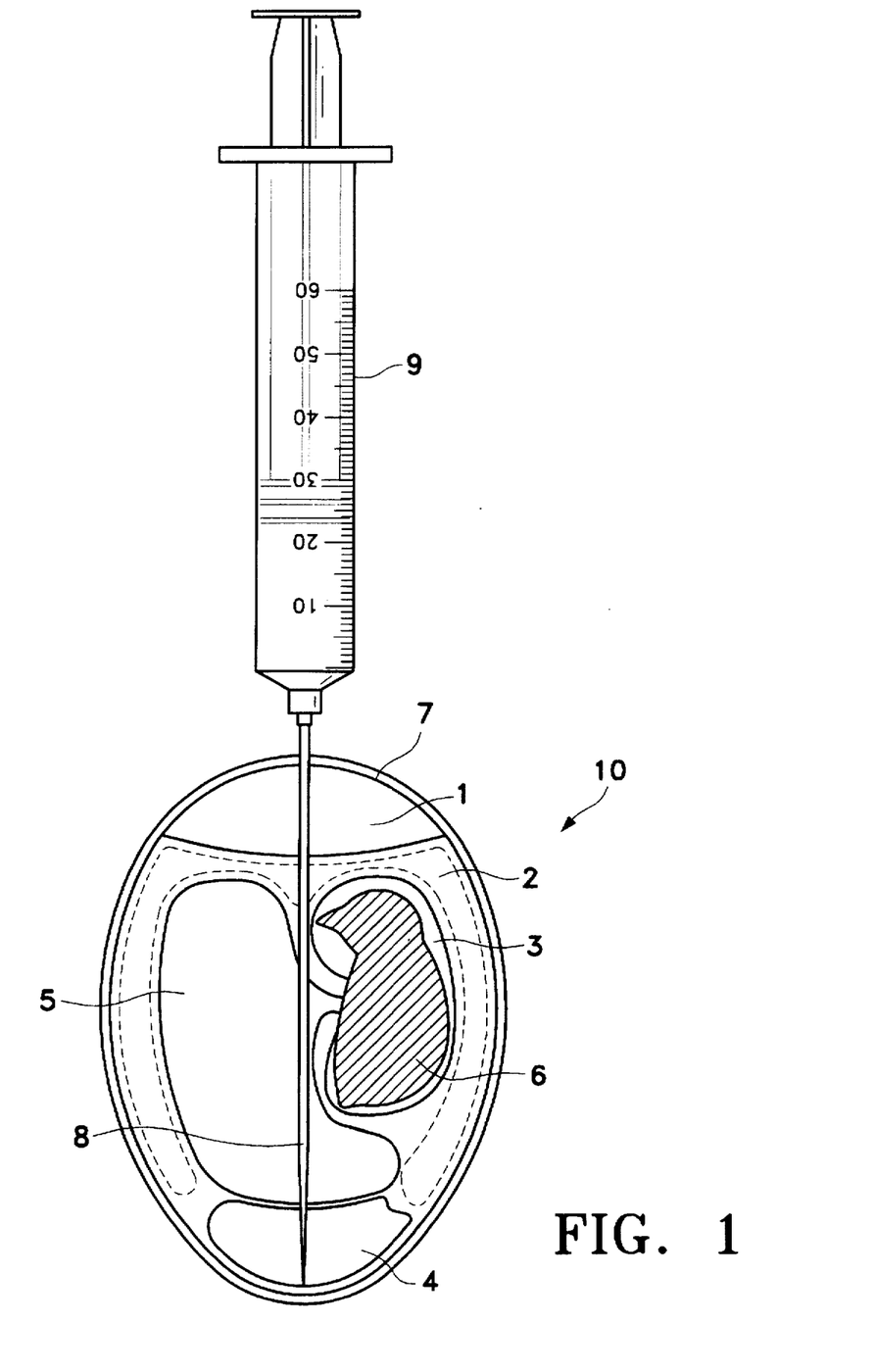
FIG. 1 shows a cross-section of chicken embryo 6 air cell end 1 up illustrating how needle 8 is placed in albumin 4 where the vaccine is deposited. The embryo 6 in the illustration is younger than when the injection actually is administered.
Figure 2A:
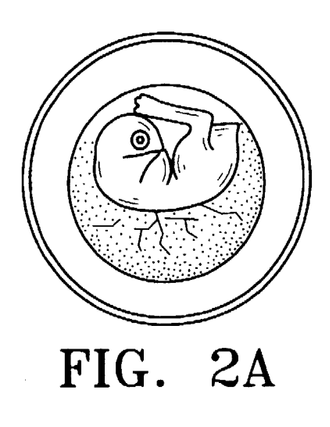
FIG. 2A shows an embryo of 9 to 10 days of age.
Figure 2B:
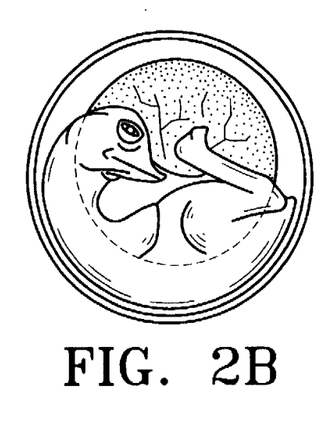
FIG. 2B shows a 13 day embryo.
Figures 2C, 2E:
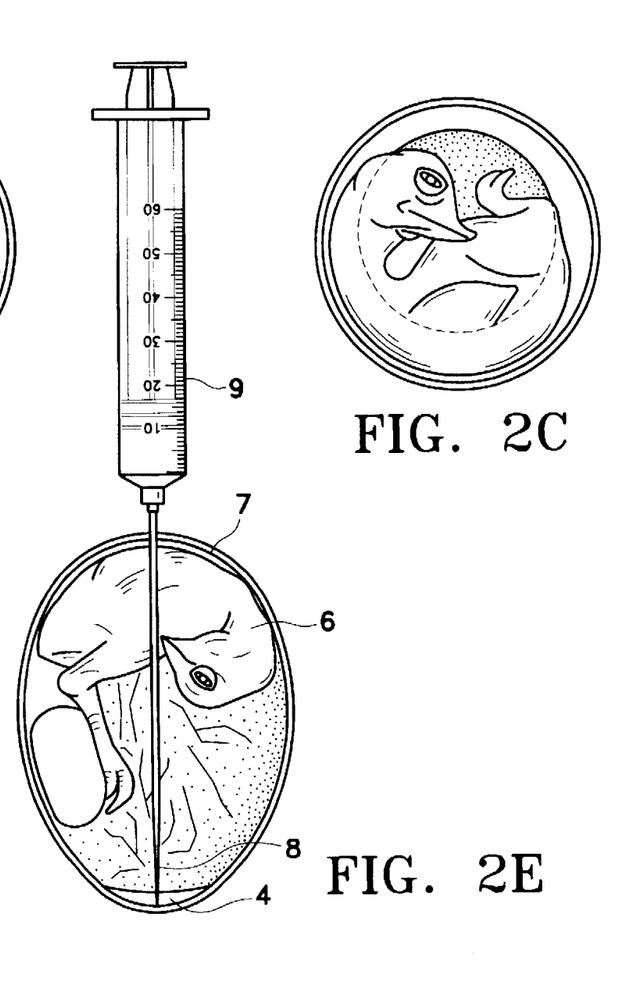
FIG. 2C shows a 15 day embryo.
FIG. 2E shows an 18 day embryo being vaccinated.
Figure 2D:
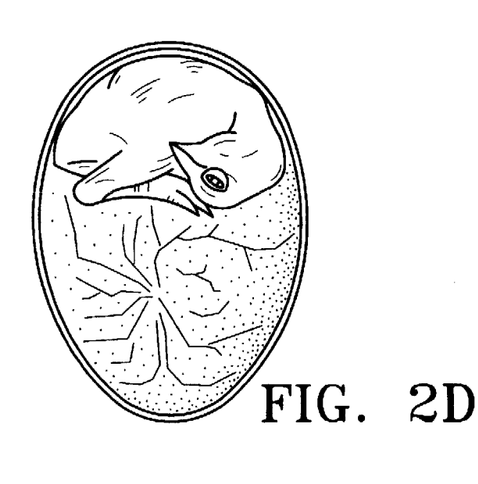
FIG. 2D shows a 17 day embryo.
Figure 3A:
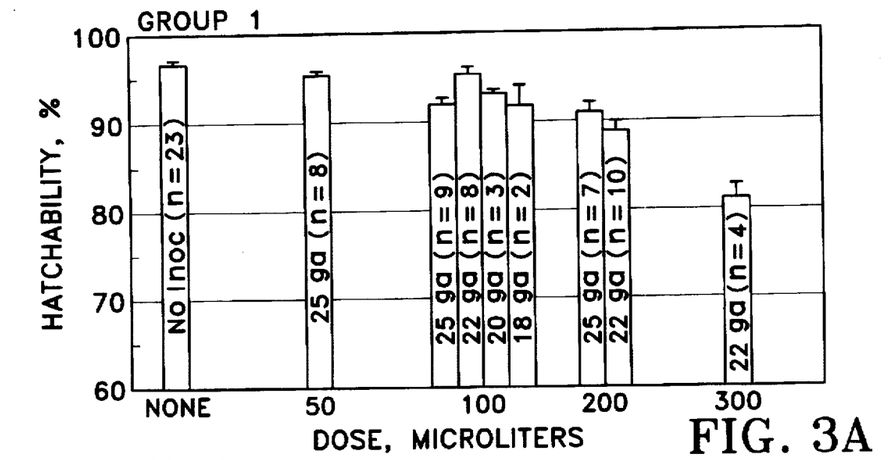
FIGS. 3a–3c are a series of graphs showing percent hatchability of white leghorn chickens vaccinated in ovo at day 18 with Newcastle Disease (ND) virus oil emulsion vaccines using different gauge needles and different doses in microliters.
Figure 3B:
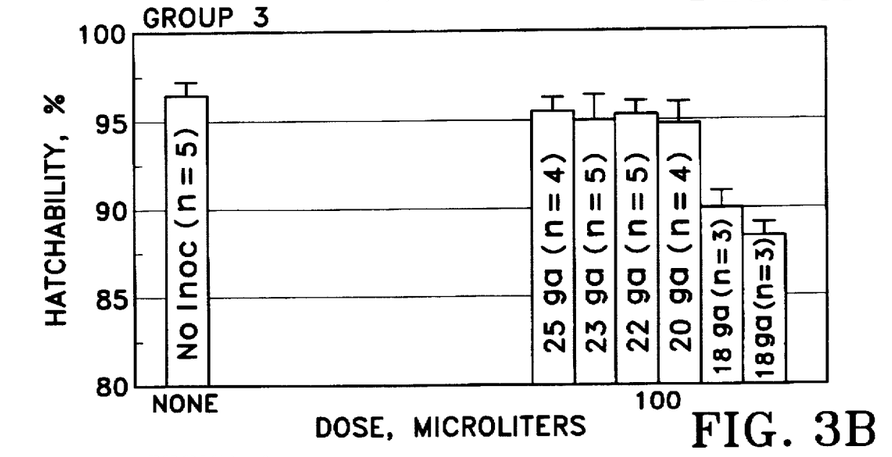
Figure 3C:
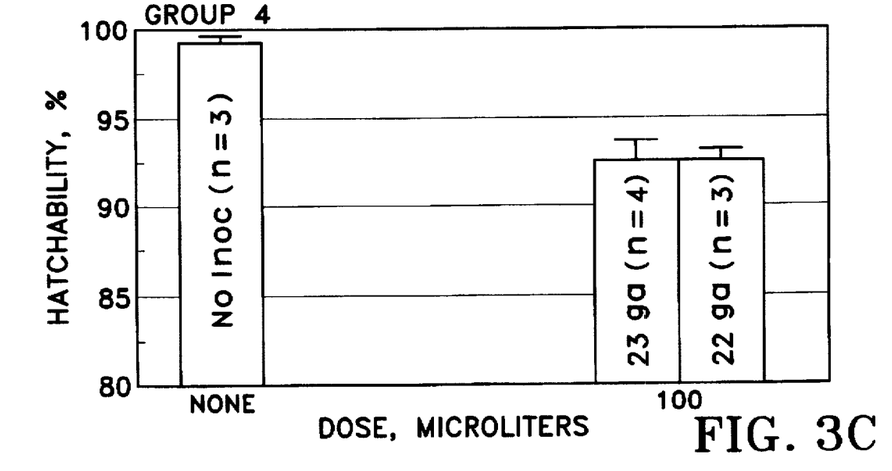
Figure 4A:
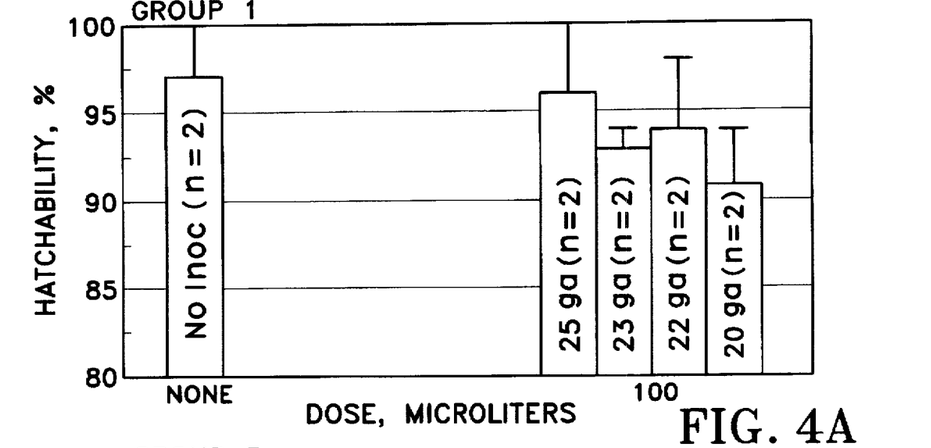
FIGS. 4a–4c are graphs showing percent hatchability of white rock chickens vaccinated in ovo at day 18 using different gauge needles at a dose of 100 microliters with a Newcastle Disease virus oil emulsion vaccine.
Figure 4B:
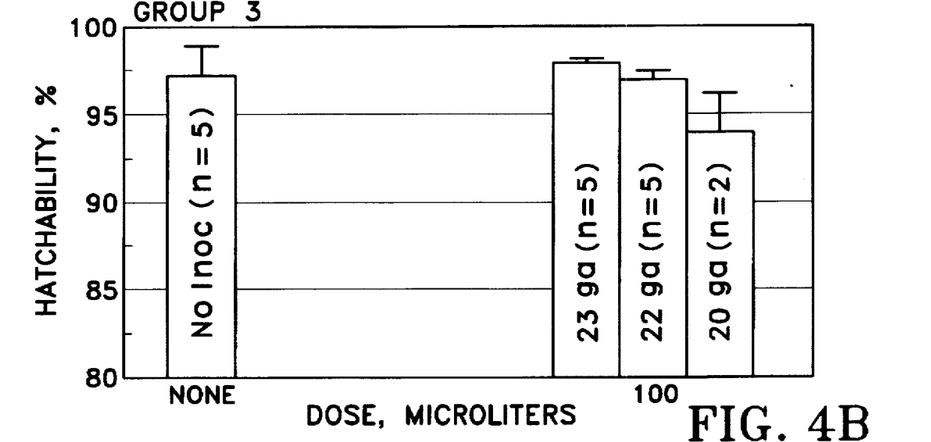
Figure 4C:
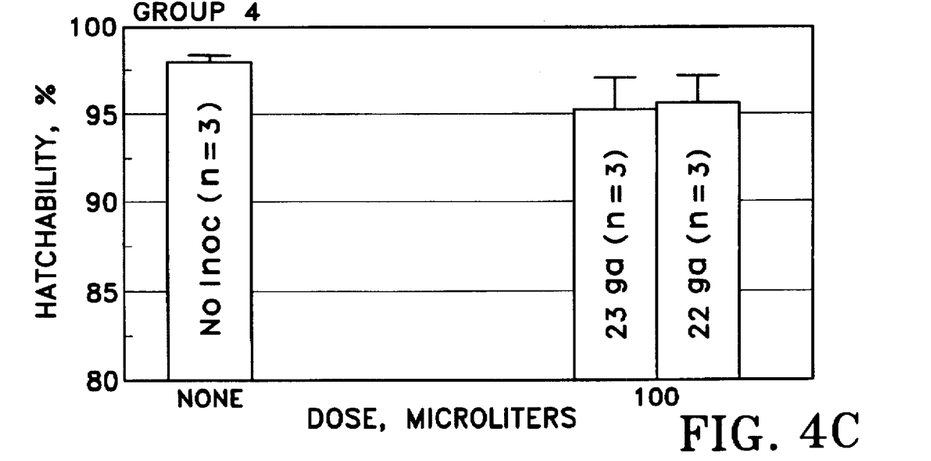

The mechanism of injection is not particularly critical provided it does not unduly damage the tissues and organs of the embryo or the extraembryonic membranes surrounding it. A hypodermic syringe 9 fitted with a needle 8 of a gauge selected from 27, 25, 23, 22, 20, 18, and 16 gauge is suitable for the injection. A 25 gauge needle is more preferred. The length of needle 8 is dependent on the height of the egg. For example, for an average egg height of $1^{15}/_{16}$ inches, a 1½ or 1¾ inch needle would be suitable. For an average egg height of $2^{5}/_{16}$", a three inch needle would be suitable. Needle 8 is inserted vertically from the center of the large end 1 of a chicken egg 10 through the center line to the small end of the egg 4. For an average egg height of $1^{15}/_{16}$ inches, a 1½ inch needle would be fully inserted. When using a needle which is longer than the egg height, needle 8 is inserted into the large end 1 of egg to the end of the small end 4 and is withdrawn from the shell a small distance in order to push the vaccine out of the needle. One of ordinary skill in the art could readily determine the needle length based on the height of the particular avian egg that will be injected.

In an automated system, it is envisioned that a penetrating device such as, for example, that taught by Miller in U.S. Pat. No. 4,040,388 or Paul et al. in U.S. Pat. No. 5,176,101 could be modified to carry out the method of the present invention. While it would not be desirable to apply heat to the needle for sterilization purposes, as suggested in the Miller patent, to the extent of inactivating the vaccine or cooking the egg's interior, sterilization between injections would be beneficial in preventing cross-contamination.

Embryonal vaccination under the aforementioned conditions is characterized by a hatch rate greater than 80% for 18-day embryos and doses of 300 ul or less, approximately about 97% for groups injected with a 25 gauge needle, approximately about 94% for groups injected with a 23 gauge needle, approximately about 96% for groups injected with a 22 gauge needle, approximately about 91% for groups injected with a 20 gauge needle, approximately about 92% for groups injected with an 18 gauge needle, and approximately about 88% for groups injected with a 16 gauge needle. Untreated eggs have a hatch rate of greater than 95% for 18-day embryos. Furthermore, in ovo immunization with oil emulsions containing inactivated antigen confers immunity to newly hatched chicks and the vaccination persists past the hatch date.

The following examples illustrate the invention and are not intended to limit the scope of the invention as defined by the claims. A Newcastle disease virus vaccine with chick embryos is used as a test model system.

EXAMPLE 1

Embryonating eggs of specific-pathogen-free (SPF) white rock and white leghorn chickens were from the USDA, Agricultural Research Services' Southeast Poultry Research Laboratory flocks which are free of Newcastle Disease, avian leukosis, infectious bursal disease, adenovirus disease, reovirus, pox, laryngotracheitis, reticuloendotheliosis, infectious coryza, fowl typhoid, fowl cholera, salmonella, avian influenza, infectious bronchitis, mycoplasma, Marek's disease, and avian encephalomyelitis antibodies. Eggs, to be incubated, were collected twice daily, held at approximately about 50°–55° F. until set, then at approximately about 99.5±5° F. and approximately about 55±0.5% relative humidity, and selected for cleanliness. Groups of vaccinated eggs were placed and hatched in separate enclosed wire hatching cages in an incubator at approximately about 99.5° F. and approximately about 55% relative humidity. Hatched chicks from each group were wing banded for identification at 1-day-old, transferred, and mixed with other hatchmate groups in a brooder battery. Chickens losing wing bands were killed and discounted from their groups. They had access to a 95° F. heated area with feed and water available ad libidum for two weeks and then were transferred to growing batteries. Chickens were housed in disease containment buildings with filtered air and temperature control (70° F.). Serum samples were collected at 1-week intervals from all chickens beginning 2 weeks posthatch for Hemagglutination-inhibition (HI) tests. Noninjected control eggs were used as an indication of normal hatch rates.

EXAMPLE 2

Ulster Newcastle disease virus (NDV) in allantoic fluid (hemagglutinin [HA] titer=1600, 50% embryo-lethal-dose $[ELD_{50}]=10^{9.1}/0.1$ ml) was propagated in 9-day-old embryos until 50% or more died, then virus containing allantoic fluid was harvested, pooled, and inactivated with 0.1% beta-propiolactone (BPL) for approximately about 2–4 hours at approximately about 24° C., and frozen (−20° C.) until used. The inactivated virus is also referred to as the antigen. Inactivation of NDV was confirmed by embryo inoculation. The antigen was also used for the hemagglutination-inhibition (HI) tests. The same antigen was used for all experiments and was undiluted.

MBL #1, an experimental Bursal Disease antigen vaccine (Maine Biological Laboratories, Inc., China Road, P.O. Box 225, Waterville, Me., 04903-0255) is prepared by growing the antigen in young chicks from which bursa, spleen, and thymus are removed after infection with infectious bursal disease, milled, inactivated, and emulsified into a mineral oil vaccine using a commercial emulsifying machine.

MBL #2 is an experimental Newcastle Disease Virus vaccine (Maine Biological Laboratories, Inc.) prepared by growing the virus in chick embryos. The embryos are finely ground and the virus inactivated. The ground tissue is then emulsified into a mineral oil vaccine using a commercial emulsifying machine. This Newcastle Disease virus is a different strain then the Ulster strain above.

Avian influenza (AI) strain A/Turkey/Wisconsin/68 (H5N9) is propagated in the allantois of 9-day-old embryonating chicken eggs by inoculation of approximately $10^3$ fifty percent egg infective doses ($EID_{50}$) of virus. The eggs are incubated for approximately about 48 hours at 37° C. and are chilled to 4° C. before allantoic fluids are harvested. The allantoic fluids contain approximately about $10^{8.9}$ embryo-lethal dose$_{50}$/0.1 ml and have a hemagglutination titer of 1:1600. Inactivation of the fluids for antigen is by treatment with 0.1% beta-propiolactone for 4 hours at approximately about 24° C. The absence of residual infectivity was confirmed by egg inoculation. The antigen is used unconcentrated and is kept at −20° C. until use. No preservatives are added to the preparation.

Avian influenza (AI) strain A/Turkey/Wisconsin/68 (H5N2) is an experimental vaccine from Maine Biological Laboratories prepared as described above for the (H5N9) Avian Influenza virus vaccine.

Salmonella enteritidis (SE) strain SE-E6 is grown up in an overnight culture of tryptic soybroth (TSB) culture. The cultures were set up as three 1.5 liter/flask cultures, each inoculated with approximately about 0.3 ml of loop picked SE from overnight nutrient agar plates. Broths are incubated at approximately about 39° C. overnight. The cultures are centrifuged to pellet the bacteria. The pellets are resuspended in 200 ml phosphate-buffered saline (PBS) and divided into 9 aliquots. Each aliquot is washed twice in PBS and the pelleted bacteria is inactivated with 10 ml of acetone for approximately about 2 hours at room temperature with occasional resuspension. Most of the acetone is removed by pipetting and the remainder is eliminated by evaporation in a desiccator under vacuum. Each tube is equivalent to 500 ml of culture. The SE antigen is kept at -20° C. until use. The antigen is diluted with PBS and the vaccine prepared as described in Example 3.

To form concentrated antigen for vaccines, the antigen preparation is concentrated by centrifugation into a button by spinning the virus down for two hours at 20,000 rpm. The button is resuspended into a smaller volume of fluid such as 1/20 to get a 20× concentration, 1/10 for 10×, etc.

EXAMPLE 3

Water-in-oil emulsion vaccine was prepared with both oil-soluble surfactant, Arlacel 80 (Sorbitan monooleate) and water-soluble surfactant, Tween 80 (Polysorbate 80) added to mineral oil in a total content of 10% and a ratio of 3 parts Arlacel to 1 part Tween. This ratio of surfactants provides a hydrophile-lipophile balance (HLB) of 7.0 for best efficacy and is used for all vaccines unless otherwise indicated. See Schick, Nonionic Surfactants, Marcel Dekker, Inc., New York, N.Y., 609–611, 1966, which is herein incorporated by reference. The oil phase (oil plus surfactants) was autoclaved before vaccine emulsification. The mineral oil was Drakeol 6VR (Penreco Butler, Pa.). Oil phase to aqueous antigen (aqueous phase is allantoic fluid for NDV and AI; PBS for SE) was 4:1 for all vaccines unless indicated otherwise.

Newcastle Disease virus metabolizable oil vaccines are prepared as described in U.S. patent application Ser. No. 08/384,184 (herein incorporated by reference).

Multivalent (polyvalent) vaccines were prepared by mixing equal parts of the monovalent vaccines together.

EXAMPLE 4

Vaccine efficacy for viral antigens is evaluated based on hemagglutination-inhibition (HI) antibody levels in serum of post-hatch chickens. HI antibody levels were determined by the microtest procedure described in Beard et al., Proceedings of the 77th Annual Meeting U.S. Animal Health Association, 596–600, 1973, which is herein incorporated by reference; using 8 HA units of NDV antigen. SE titers were determined by a SE microagglutination test described in Gast et al., Avian Diseases, vol. 34, 721–728, 1990, which is herein incorporated by reference. HI titers for ND and AI of 1:40 or above were considered indicative of protection induced by the vaccine against death. Seroconversion is also determined on the collected serum. Tests were conducted the day serum samples were taken.

EXAMPLE 5

Groups of embryonating white leghorn and white rock chicken eggs 10 were punctured at the longitudinal midline over the air cell 7 with an egg punch and injected with mineral oil emulsion vaccine using different doses between 25 ul and 600 ul (See Tables 1, 2, 3, and 4) in the small end of the egg. The shell holes were not sealed. HI tests were conducted weekly at 2 weeks–9 weeks post hatch and at week 11.

The different variables include length of needle 8 using same average egg height (see Tables 1 and 2), in the orientation of the egg while the vaccine was being administered into the small end 4 of the egg via the large end 1, the point of entry in the egg. An HI titer of 3 or higher is considered protective. Furthermore, embryonating white leghorn chicken eggs were vaccinated as 18-day-old embryos directly through the small end 4 at different depths. The results are shown in Tables 1–5.

TABLE 1

Hemagglutination-inhibition (HI) titers post-hatch of white leghorn chickens vaccinated as 18-day-old embryos.

| Group no. | ul dose | # in group | # resp. | HI GMT weeks post-hatch of responders | | | | | | | | | |
|---|---|---|---|---|---|---|---|---|---|---|---|---|---|
| | | | | 2 | 3 | 4 | 5 | 6 | 7 | 8 | 9 | 11 | X |
| 1 | 25 | 11 | 4 | 5.0 | 4.5 | 4.7 | 4.0 | 5.0 | — | — | — | — | 4.6 |
| 2 | 50 | 5 | 2 | 3.7 | 6.0 | 6.5 | 6.3 | 5.2 | — | — | — | — | 5.5 |
| 3 | 100 | 8 | 8 | 3.2 | 5.6 | 6.1 | 5.9 | 6.0 | 5.9 | — | — | — | 5.5 |
| 4 | 150 | 4 | 4 | 4.0 | 6.2 | 5.4 | 6.2 | 6.2 | 6.2 | — | — | — | 5.7 |
| 5 | 200 | 10 | 10 | 4.1 | 6.4 | 6.9 | 7.1 | 6.9 | 7.2 | — | — | — | 6.4 |
| 6 | 250 | 11 | 10 | 4.7 | 6.7 | 7.7 | 7.7 | 7.7 | 7.2 | 7.3 | — | — | 7.0 |
| 7 | 400 | 10 | 8 | 2.8 | 6.9 | 7.7 | 8.3 | 8.3 | 8.4 | 9.0 | 9.1 | 8.7 | 7.7 |
| 8 | 500 | 3 | 3 | 5.6 | 6.3 | 6.7 | 6.7 | 6.7 | 6.7 | — | — | — | 6.5 |
| 9 | 600 | 2 | 2 | 4.0 | 7.5 | 8.0 | 8.5 | 8.5 | 8.0 | — | — | — | 7.4 |
| 10 | none | 3 | 0 | <1 | <1 | <1 | <1 | <1 | <1 | — | — | — | <1.0 |

HI titer of 1 = 1:10, 4 = 1:80, 6 = 1:320, etc.

Notes:
1. Vaccine was Drakeol 6VR with 10% Arlacel and Tween 80 at HLB 7.0. O/A was 4:1.
2. Injection was vertical from large end through center line to small end.
3. Injection was 1½ inches with 22-gauge needle.
4. Egg height was 1 15/16 inches average.
5. Hole for injection was not sealed.

TABLE 2

Hemagglutination-inhibition (HI) titers post-hatch of white leghorn chickens vaccinated as 18-day-old embryos.

| Group no. | ul dose | # in group | # resp. | HI GMT weeks post-hatch of responders | | | | |
|---|---|---|---|---|---|---|---|---|
| | | | | 2 | 3 | 4 | 5 | X |
| 1 | 100 | 10 | 8 | 3.9 | 4.3 | 6.0 | 6.3 | 5.1 |
| 2 | 200 | 9 | 6 | 4.5 | 5.7 | 6.3 | 6.5 | 5.8 |
| 3 | 300 | 8 | 7 | 3.8 | 6.9 | 7.1 | 7.1 | 6.2 |
| 4 | 400 | 3 | 3 | 4.5 | 6.5 | 6.7 | 6.0 | 5.9 |
| 5 | 500 | 9 | 9 | 4.6 | 6.6 | 8.1 | 7.4 | 6.7 |
| 6 | 200 | 11 | 8 | 4.3 | 6.1 | 7.4 | 7.3 | 6.3 |
| 7 | 300 | 7 | 6 | 3.8 | 6.6 | 6.7 | 6.5 | 5.9 |
| 8 | 400 | 7 | 6 | 4.2 | 5.2 | 7.0 | 6.7 | 5.8 |
| 9 | 500 | 2 | 2 | 4.0 | 6.5 | 7.0 | 7.0 | 6.1 |
| 10 | control | 3 | 0 | <1 | <1 | <1 | <1 | <1.0 |

HI titer of 1 = 1:10, 4 = 1:80, 6 = 1:320, etc.
Notes:
1. Vaccine was Drakeol 6VR with 10% Arlacel and Tween 80 at HLB 7.0. O/A was 4:1.
2. Group nos. 1–5 were injected with 1½ inch 22-gauge needles. Group nos. 6–9 were injected with 1¾ inch 22-gauge needles.
3. Egg height was 1$^{15}$/$_{16}$ inches average.
4. Injection was as in Table 1.
5. Hole for injection was not sealed.

TABLE 3

Hemagglutination-inhibition (HI) titers post-hatch of white rock chickens vaccinated as 18-day-old embryos.

| Group no. | ul dose | # in group | # resp. | HI GMT weeks post-hatch of responders | | | | |
|---|---|---|---|---|---|---|---|---|
| | | | | 2 | 3 | 4 | 5 | X |
| 1 | 100 | 19 | 13 | 4.4 | 4.5 | 6.0 | 5.2 | 5.0 |
| 2 | 200 | 20 | 16 | 4.2 | 5.0 | 6.3 | 6.3 | 5.5 |
| 3 | 300 | 19 | 13 | 3.8 | 4.4 | 6.0 | 6.1 | 5.1 |
| 4 | 400 | 15 | 10 | 5.1 | 6.0 | 8.4 | 6.7 | 6.6 |
| 5 | 500 | 13 | 11 | 5.0 | 6.5 | 7.6 | 8.0 | 6.8 |
| 6 | 200 | 18 | 12 | 3.0 | 5.3 | 5.9 | 5.2 | 4.9 |
| 7 | 200 | 15 | 9 | 2.9 | 5.1 | 5.8 | 5.2 | 4.8 |
| 8 | 200 | 20 | 12 | 5.2 | 5.9 | 6.3 | 6.4 | 6.0 |
| 9 | 1000 | 6 | 3 | 6.9 | 8.0 | 7.3 | 7.7 | 7.5 |
| 10 | 300 | 11 | 9 | 4.8 | 6.6 | 7.1 | 7.5 | 6.5 |
| 11 | none | 20 | 0 | <1 | <1 | <1 | <1 | <1.0 |

HI titer of 1 = 1:10, 4 = 1:80, 6 = 1:320, etc.
Notes:
1. Vaccine and injection was the same as in Table 1.
2. Egg height was 2$^{15}$/$_{16}$ inches average.
3. Group no. 6 was vaccinated from top to bottom of shell with 3-inch needle.
4. Group no. 7 was vaccinated as in No. 6 with egg inverted.
5. Group no. 8 was vaccinated as in No. 2 with egg inverted.

TABLE 3-continued

Hemagglutination-inhibition (HI) titers post-hatch of white rock chickens vaccinated as 18-day-old embryos.

| Group no. | ul dose | # in group | # resp. | HI GMT weeks post-hatch of responders | | | | |
|---|---|---|---|---|---|---|---|---|
| | | | | 2 | 3 | 4 | 5 | X |

6. Group no. 9 was vaccinated as in No. 6 with egg inverted.
7. Group no. 10 was vaccinated as in No. 3 with egg inverted.

TABLE 4

Hemagglutination-inhibition (HI) titers post-hatch of white rock chickens vaccinated as 18-day-old embryos with ND oil emulsion vaccine.

| Group no. | ul dose | # in group | # resp. | HI GMT weeks post-hatch of responders | | | |
|---|---|---|---|---|---|---|---|
| | | | | 2 | 3 | 4 | X |
| 1 | 100 | 18 | 5 | 2.0 | 4.2 | 5.4 | 3.9 |
| 2 | 200 | 15 | 6 | 3.0 | 6.3 | 6.3 | 5.2 |
| 3 | 300 | 14 | 5 | 3.5 | 5.0 | 5.8 | 4.8 |
| 4 | 400 | 12 | 9 | 3.8 | 7.0 | 7.0 | 5.9 |
| 5 | 500 | 11 | 8 | 3.4 | 4.5 | 6.3 | 4.7 |
| 6 | 1000 | 5 | 4 | 7.0 | 6.5 | 6.5 | 6.7 |
| 7 | 300 | 10 | 5 | 3.3 | 5.2 | 4.0 | 4.2 |
| 8 | 300 | 11 | 6 | 5.2 | 7.0 | 7.0 | 6.4 |
| 9 | none | 18 | 0 | 0.0 | 0.0 | 0.0 | 0.0 |

HI titer of 1 = 1:10, 2 = 1:20, 3 = 1:40, 4 = 1:80, 5 = 1:160, 6 = 1:320, 7 = 1:640
HI titers of 1:40 or above are considered protective
Notes:
1. Injection was perpendicular from the large end of egg through the mid-line to the bottom inside surface of the small end.
2. Needles were 22-gauge, 3-inches long.
3. In group No. 7 the eggs were inverted then injected as described in Example 5.
4. In group No. 8 the eggs were injected horizontally from large end to small end.
5. Flock was at end of lay.
6. Egg height 2$^5$/$_{32}$".

TABLE 5

Hemagglutination-inhibition (HI) titers post-hatch of white leghorn chickens vaccinated as 18-day-old embryos with Newcastle Disease (ND) oil-emulsion (OE) vaccine given at different depths through the small end.

| Group Number | Depth of Inj. | Total CE Inj. | No. Hatch | % Hatch | # per Group | No. Repose | % Response | Geometric Mean HI Titers Weeks (posthatch) | | | Mean Titer |
|---|---|---|---|---|---|---|---|---|---|---|---|
| | | | | | | | | 2 | 3 | 4 | |
| 1 | ¼" | 20 | 19 | 95 | 15 | 0 | 0 | 0.0 | 0.0 | 0.0 | 0.0 |
| 2 | ½" | 20 | 18 | 90 | 15 | 5 | 33 | 4.0 | 4.8 | 4.8 | 4.5 |
| 3 | 1" | 20 | 16 | 80 | 15 | 10 | 67 | 4.4 | 5.6 | 5.6 | 5.2 |
| 4 | 1½" | 20 | 18 | 90 | 15 | 8 | 53 | 3.9 | 4.9 | 5.4 | 4.7 |

TABLE 5-continued

Hemagglutination-inhibition (HI) titers post-hatch of white leghorn chickens vaccinated as 18-day-old embryos with Newcastle Disease (ND) oil-emulsion (OE) vaccine given at different depths through the small end.

| Group Number | Depth of Inj. | Total CE Inj. | No. Hatch | % Hatch | # per Group | No. Reponse | % Response | Geometric Mean HI Titers Weeks (posthatch) | | | Mean Titer |
|---|---|---|---|---|---|---|---|---|---|---|---|
| | | | | | | | | 2 | 3 | 4 | |
| 5 | None-Ctrl | 25 | 24 | 96 | 24 | 0 | 0 | 0.0 | 0.0 | 0.0 | 0.0 |

Notes:
1. Needles were 20 gauge ¼", ½", 1", and 1½" respectively for groups 1, 2, 3, and 4.
2. Egg fluid was expelled when vaccine was administered at ¼", ½" and 1" depths.
3. Eggs were vertical with small end up.
4. Holes were not sealed.
5. Vaccine dose was 100 ul.

EXAMPLE 6

52-day-old white leghorn chickens were challenged with the lethal Fontana strain of velogenic viscerotropic Newcastle disease virus (VVNDV) at 8 weeks post-vaccination as 18-day-old embryos. The embryos received a 200 ul dose of the mineral oil emulsion with Ulster NDV antigen prepared as described in Examples 2 and 3 above. The mean HI titer at the time of challenge was 7.2. Individual post-hatch titers of each of the ten chickens is reported in Table 5 below. VVNDV was given intraocularly in a 0.1 ml volume containing $10^{7.3} ELD_{50}$. Chickens were observed over a two week period for morbidity and mortality. Vent and tracheal swabs were taken 5 and 14 days postchallenge for virus isolation and HI titers were determined as described above. The results are reported in Table 6 below.

EXAMPLE 7

At the end of the experiments, all in ovo vaccinated chickens were sacrificed and examined in the abdominal cavity or the breast muscle for the formation of lesions which were induced by the immunization. A lesion is defined as discolored, demarcated, inflamed, edematous, granulomatous, indurated, or necrotic tissue; or if tissue contained either encapsulated or diffuse vaccine. Usually, when a newly hatched chicken is vaccinated using a mineral oil emulsion vaccine, lesions appear as early as three weeks. In the in ovo immunized chickens, there was no evidence of gross lesions in any of the meat even after 11 weeks post-hatch. None of the meat would have been condemned for meat consumption.

EXAMPLE 8

The HI titers of post-hatch white leghorn chickens vaccinated in ovo were compared to that of chicks vaccinated at 1-day-old. 18-day and 19-day embryos as well as 1-day-old chicks were vaccinated with 200 ul of the Newcastle disease oil-emulsion vaccine prepared as described in Examples 2 and 3 above. 1-day old chicks received 200 ul of the vaccine subcutaneously in the nape of the neck region. 18-day and 19-day embryos were vaccinated as described in Example 5. The results are reported in Table 7 below.

TABLE 6

Challenge response of 52-day-old white leghorn chickens to velogenic viscerotropic Newcastle disease (VVNDV) at 8-weeks postvaccination as 18-day-old embryos.

| Chicken Number | HI titer at weeks post-hatch | | | | | | Mean titer | Virus isolation | | No. alive/Total no. | |
|---|---|---|---|---|---|---|---|---|---|---|---|
| | 2 | 3 | 4 | 5 | 6 | 7 | | oral | cloaca | controls | vaccination |
| 1 | 3 | 8 | 8 | 8 | 8 | 8 | 7.2 | − | − | 0/5 | 10/10 |
| 2 | 4 | 4 | 5 | 5 | 5 | 6 | 4.8 | + | − | | |
| 3 | 4 | 7 | 6 | 5 | 6 | 6 | 5.7 | + | − | | |
| 4 | 4 | 8 | 8 | 9 | 8 | 8 | 7.5 | + | − | | |
| 5 | 4 | 8 | 8 | 8 | 8 | 8 | 7.3 | + | − | | |
| 6 | 6 | 7 | 6 | 6 | 6 | 6 | 6.2 | − | − | | |
| 7 | 4 | — | 7 | 7 | 6 | 6 | 6.0 | + | − | | |
| 8 | 6 | 8 | 8 | 9 | 8 | 9 | 8.0 | + | − | | |
| 9 | 6 | 8 | 8 | 9 | 8 | 9 | 8.0 | − | − | | |
| 10 | <1 | <1 | 5 | 5 | 5 | 6 | 3.5 | + | − | | |
| | | | | | | | | 7/10 | 0/10 | | |
| controls | | | | | | | | | | | |
| 11 | <1 | <1 | <1 | <1 | <1 | <1 | <1.0 | ND | ND | | |

Notes:
1. Challenge was $10^{7.3}$ VVNDV in 0.1 ml given intraocularly.
2. Observation period was 2 weeks.
3. Virus isolation attempts were made at 5 days postchallenge.
4. There was no morbidity in the vaccinates.
5. Vaccine dose was 0.2 ml of mineral oil emulsion with Ulster NDV (0.1% BPL).
6. All unvaccinated controls died.

TABLE 7

Hemagglutination-inhibition (HI) titers post-hatch of white leghorn chickens vaccinated as 18- or 19-day-old chick embryos (CE) or 1-day-old chicks with Newcastle Disease (ND) oil-emulsion vaccine.[A]

| Group Number | No. CE | No. Hatch | % Hatch | No. Response/ Total | Percent Response | Geometric Mean HI Titers of Responders — Weeks (posthatch) | | | | | Mean Titer |
|---|---|---|---|---|---|---|---|---|---|---|---|
| | | | | | | 2 | 3 | 4 | 5 | 6 | |
| TRIAL 1 | | | | | | | | | | | |
| 1 Antigen only | 20 | 19 | 95 | 0/19 | 0 | 0.0 | 0.0 | 0.0 | 0.0 | — | 0.0 |
| 2 18-day-CE | 20 | 17 | 85 | 10/17 | 59 | 4.6 | 4.9 | 7.0 | 6.8 | — | 5.8 |
| 3 19-day-CE | 20 | 16 | 80 | 9/16 | 56 | 3.9 | 6.5 | 5.6 | 5.6 | — | 5.4 |
| 4 1-day-chick | 20 | 20 | 100 | 18/20 | 90 | 4.3 | 7.8 | 7.5 | 7.6 | — | 6.8 |
| 5 No vacc. Ctrl. | 20 | 18 | 90 | 0/18 | 0 | 0.0 | 0.0 | 0.0 | 0.0 | — | 0.0 |
| 6 Needle only injection | 20 | 17 | 85 | ND | — | — | — | — | — | — | — |
| TRIAL 2 | | | | | | | | | | | |
| 7 18-day-CE | 20 | 17 | 85 | 10/15 | 67 | 5.0 | 5.6 | 6.2 | 6.4 | 6.2 | 5.9 |
| 8 1-day-chick | 10 | 10 | 100 | 10/10 | 100 | 5.2 | 6.8 | 7.8 | 7.9 | 7.6 | 7.1 |
| 9 No vacc. Ctrl. | 20 | 20 | 100 | 0/20 | 0 | 0.0 | 0.0 | 0.0 | 0.0 | 0.0 | 0.0 |

[A]Embryos received 200 ul of vaccine full depth on center line from large end to small end of egg. One-day-old chicks received 200 ul of vaccine subcuteneously in nape of neck region.

EXAMPLE 9

White rock chicken embryos from flocks at the beginning of lay and flocks at the end of lay were vaccinated at 14 to 18 days using different amounts of the vaccine preparation described in Examples 2 and 3 above and in different oil phase/aqueous antigen (O/A) ratios (see Tables 8 and 9 below). The vaccine was also placed at different depths in the egg. The results are shown in Tables 8 and 9 below.

TABLE 8

Hemagglutination-inhibition (HI) titers post-hatch of white rock chickens vaccinated as embryos at 18 days at different depths with Newcastle disease (ND) oil-emulsion vaccine.

| Group Number | Percent Hatch | No. Tested | % Resp. | Depth of Injection | Percent Avg. Depth in Egg | ul Dose | Vaccine O/A Ratio | HI GMT weeks posthatch of responders | | | |
|---|---|---|---|---|---|---|---|---|---|---|---|
| | | | | | | | | 3 | 4 | 5 | X |
| 1 | 79 | 13 | 92 | 1½ | 76 | 200 | 4:1 | 6.4 | 6.9 | 6.2 | 6.5 |
| 2 | 85 | 18 | 89 | 1¾ | 89 | 200 | 4:1 | 6.8 | 7.5 | 7.1 | 7.1 |
| 3 | 85 | 18 | 89 | 2 | 100 | 200 | 4:1 | 6.7 | 7.0 | 7.0 | 6.9 |
| 4 | 85 | 16 | 69 | full | 100 | 200 | 4:1 | 5.3 | 5.6 | 6.6 | 5.8 |
| 5 | 100 | 20 | 94 | 1½ | 76 | 200 | 60:40 | 7.4 | 8.1 | 7.6 | 7.7 |
| 6 | 90 | 17 | 100 | 1¾ | 89 | 200 | 60:40 | 8.2 | 7.5 | 6.9 | 7.5 |
| 7 | 70 | 17 | 65 | 2 | 100 | 200 | 60:40 | 5.3 | 6.7 | 7.2 | 6.4 |
| 8 | 100 | 19 | 80 | full | 100 | 200 | 60:40 | 6.1 | 6.8 | 5.5 | 6.1 |
| 9 | 80 | 6 | 67 | 1¾ | 89 | 300 | 4:1 | 7.0 | 8.0 | 7.0 | 7.3 |
| 10 | 90 | 15 | 71 | 2 | 100 | 300 | 4:1 | 7.1 | 7.5 | 7.2 | 7.3 |
| 11 | 95 | 17 | 88 | 1¾ | 89 | 300 | 60:40 | 6.9 | 7.5 | 7.3 | 7.2 |
| 12 | 70 | 10 | 83 | 2 | 100 | 300 | 60:40 | 5.6 | 7.4 | 5.6 | 6.2 |
| 13-Ctrl | 100 | — | — | — | — | — | — | — | — | — | — |

HI titer of 1 = 1:10, 2 = 1:20, 3 = 1:40, etc.
Notes:
1. Flock was at beginning of lay.
2. Injection was from large end in center line to small end of egg.
3. 22-gauge, 3-inch needles.
4. Egg height was 1³¹⁄₃₂" average.
5. Vaccine was Drakeol 6VR HLB 7, 10% (Arl 80 and Tween 80) in oil phase, O:A = 4:1, Ulster NDV.

TABLE 9

Hemagglutination-inhibition (HI) titers post-hatch of white rock chickens vaccinated as embryos at 14 to 18 days and at different depths with Newcastle disease (ND) oil-emulsion vaccine.

| No. & age of group | No. Eggs Per Group | % Hatch | No. Hatched | No. Tested | Percent Responders | Depth of Injection | Percent Average Depth of Egg | HI GMT weeks posthatch of responders | | | |
|---|---|---|---|---|---|---|---|---|---|---|---|
| | | | | | | | | 2 | 3 | 4 | X |
| 1. 14-day | 16 | 44% | 7 | 6 | 0.0 | Full | 100 | 0.0 | 0.0 | 0.0 | 0.0 |
| 2. 15-day | 20 | 70% | 14 | 10 | 20.0 | Full | 100 | 4.5 | 5.0 | 6.0 | 5.2 |

TABLE 9-continued

Hemagglutination-inhibition (HI) titers post-hatch of white rock chickens vaccinated as embryos at 14 to 18 days and at different depths with Newcastle disease (ND) oil-emulsion vaccine.

| No. & age of group | No. Eggs Per Group | % Hatch | No. Hatched | No. Tested | Percent Responders | Depth of Injection | Percent Average Depth of Egg | HI GMT weeks posthatch of responders 2 | 3 | 4 | X |
|---|---|---|---|---|---|---|---|---|---|---|---|
| 3. 16-day | 19 | 74% | 14 | 10 | 0.0 | Full | 100 | 0.0 | 0.0 | 0.0 | 0.0 |
| 4. 17-day | 18 | 72% | 13 | 11 | 36.0 | Full | 100 | 6.3 | 6.3 | 6.3 | 6.3 |
| 5. 18-day | 20 | 75% | 15 | 13 | 62.0 | Full | 100 | 4.4 | 5.5 | 5.6 | 5.2 |
| 6. 18-day | 25 | 84% | 21 | 14 | 14.0 | 1" | 46 | 2.7 | 5.6 | 5.5 | 4.6 |
| 7. 18-day | 25 | 76% | 19 | 15 | 75.0 | 1¼" | 58 | 3.7 | 5.3 | 5.1 | 4.7 |
| 8. 18-day | 25 | 80% | 20 | 17 | 71.0 | 1½" | 70 | 5.8 | 6.5 | 6.5 | 6.3 |
| 9. 18-day | 24 | 71% | 17 | 12 | 75.0 | 1¾" | 81 | 6.2 | 7.0 | 6.9 | 6.7 |
| 10. 18-day | 25 | 60% | 15 | 12 | 92.0 | 2" | 93 | 5.6 | 6.3 | 6.1 | 6.0 |
| 11. 18-day | 20 | 100% | 20 | 13 | 62.0 | ⅛" off full | 94 | 4.7 | 6.0 | 6.3 | 5.7 |
| 12. 18-day | 19 | 95% | 18 | 15 | 75.0 | ⅛" off full | 94 | 6.5 | 5.9 | 5.8 | 6.1 |
| 13. Uninoculated | 23 | 83% | 19 | — | — | — | — | — | — | — | — |

HI titer of 1 = 1:10, 2 = 1:20, 3 = 1:40, 4 = 1:80, 5 = 1:160, 6 = 1:320, 7 = 1:640
HI titers of 1:40 or above are considered protective.
Notes:
1. Vaccine dose was 0.2 ml per each egg given perpendicularly through mid-line, large end toward small end.
2. Needles were 22-gauge, 3 inches long.
3. Egg height was 2 9/32 inches average.
4. Flock was at end of lay.
5. Vaccine was mineral oil with 10% surfactant (4 parts) and 1 part NDV Ulster inactivated (0.1% BPL) antigen emulsified in a Waring blender. HLB of 7.

EXAMPLE 10

18-day-old white leghorn chick embryos (CE) were injected as described in Example 5 with varying amounts of oil emulsion vaccines containing inactivated avian influenza (AI) virus, Newcastle disease (ND) virus, and Salmonella enteritidis (SE). Furthermore, a polyvalent vaccine was prepared by mixing equal parts of the three monovalent vaccines together. The O/A ratio for all the vaccines was 4:1 and the HLB=7. The inactivated antigens were prepared as described in Example 2 above and the oil emulsion prepared as described in Example 3. Titers for AI and ND are hemagglutination titers and SE titers are microagglutination titers as described in Example 4 above. The results are reported in Table 10 below. NDV and AI titers of 1:40 or above are considered indicative of protection against death. The SE titers show sensitization has occurred and hatched chickens can be revaccinated with SE for high sustained titers.

TABLE 10

Vaccination of 18-day-old white leghorn chick embryos (CE) with monovalent and polyvalent oil emulsion (OE) of avian influenza (AI) Newcastle Disease (ND) and *Salmonella enteritidis* (SE)

| Group Number | OI Vaccine | ul Dose | No. CE Inj. | No. CE Hatch | No. Total Response | Percent Responders | GM Titers of Responders Weeks — Postvaccination 2 | 3 | 4 | 5 | Mean Titer |
|---|---|---|---|---|---|---|---|---|---|---|---|
| 1 | AI | 100 | 20 | 16 | 10/15 | 67 | 3.2 | 3.2 | 5.5 | 5.5 | 4.4 |
| 2 | AI | 200 | 20 | 17 | 08/15 | 53 | 5.4 | 5.7 | 6.3 | 7.7 | 6.3 |
| 3 | AI | 300 | 20 | 17 | 09/17 | 53 | 3.0 | 4.0 | 5.9 | 6.9 | 5.0 |
| 4 | ND | 200 | 20 | 17 | 11/15 | 73 | 4.6 | 4.9 | 7.0 | 6.8 | 5.8 |
| 5 | SE | 100 | 20 | 14 | 12/13 | 92 | 4.1 | 4.5 | 3.4 | 3.5 | 3.9 |
| 6 | SE | 200 | 20 | 18 | 14/18 | 78 | 5.0 | 5.1 | 5.0 | 4.7 | 5.0 |
| 7 | Poly (AI, ND, SE) 1:1:1v:v:v: | 300 | 20 | 17 | | | | | | | |
| | AI | 100 | | | 14/17 | 82 | 2.0 | 4.3 | 6.1 | 6.8 | 4.8 |
| | ND | 100 | | | 13/17 | 76 | 4.1 | 7.1 | 6.1 | 6.1 | 5.9 |
| | SE | 100 | | | 15/17 | 88 | 3.5 | 5.9 | 3.6 | 3.6 | 4.2 |

[A]Polyvalent vaccine was formed by adding equal parts of preformed HI, ND, and SE oil emulsion vaccines together
[B]No. of responders is the greatest no. to respond during any bleeding weeks posthatch.
[C]Titers for AI and ND are hemagglutination-inhibition titers.
Titers for SE are microagglutination titers.

EXAMPLE 11

Groups of embryonating white leghorn and white rock chicken eggs 10 were injected as described in Example 5 above with Ulster ND virus mineral oil or metabalizable oil emulsion vaccines using different doses between 50 microliters and 300 microliters and different gauge needles between 27 gauge and 16 gauge. Injection depth was 1.5 inches. Group 1 and 3 chicken embryos received a vaccine preparation as described in Example 3 to determine hatchability rates. Group 3 vaccine differs in the lot number of Arlacel 80 being a more pure preparation than the one used in group 1. Group 2 chicken embryos received a metabolizable oil emulsion vaccine as described above in Example 4. Results are shown in FIGS. 3a–3c and 4a–4c.

In pooled groups, hatchability was 97% for unvaccinated controls, 97% for groups injected with a 25 gauge needle, 94.5% for groups injected with a 23 gauge needle, 96.5% for groups injected with a 22 gauge needle, 91% for groups injected with a 20 gauge needle, 92.5% for groups injected with an 18 gauge needle, and 88% for groups injected with a 16 gauge needle.

EXAMPLE 12

Groups of embryonating white leghorn (WL) chickens were injected as described above in example 5 using a 22 gauge needle. The vaccines used were the A/turkey/Wisconsin/68 (H5N2) influenza monovalent oil emulsion vaccine, TW68, an experimental vaccine obtained from Maine Biological Laboratories, a monovalent ND oil emulsion vaccine using the ulster Newcastle Disease mineral oil emulsion vaccine described above, and 2 multivalent vaccines using experimental oil emulsion vaccine preparations, MBL #1 (Bursal Disease vaccine) and MBL #2 (Newcastle Disease vaccine) (Both from Maine Biological Laboratories, Inc.) along with the Ulster Newcastle disease antigen, prepared as described above in Example 2. Addition of Ulster Newcastle Disease vaccine to the MBL #1 and #2 demonstrates the capability to form combined vaccines of different antigens or boost the efficacy of vaccines of "like" antigens.

Figure 5:
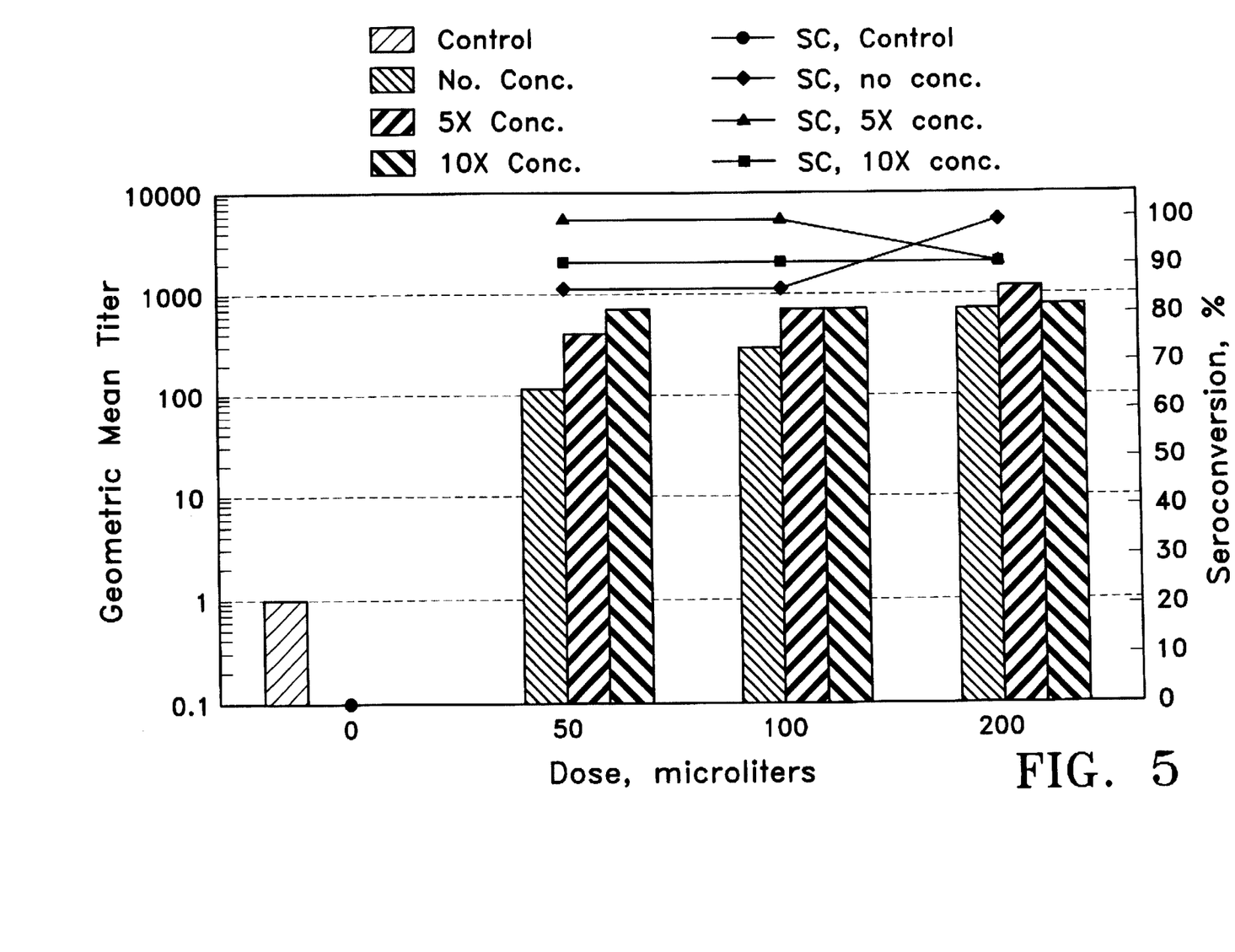
FIG. 5 is a graph showing geometric mean titers and seroconversion of white leghorn (WL) chickens vaccinated in ovo at day 18 with an experimental A/turkey/Wisconsin/ 68 influenza monovalent oil emulsion vaccine, TW68, using different concentrations of antigen and different doses in microliters using a 22 gauge needle.
Figure 6:
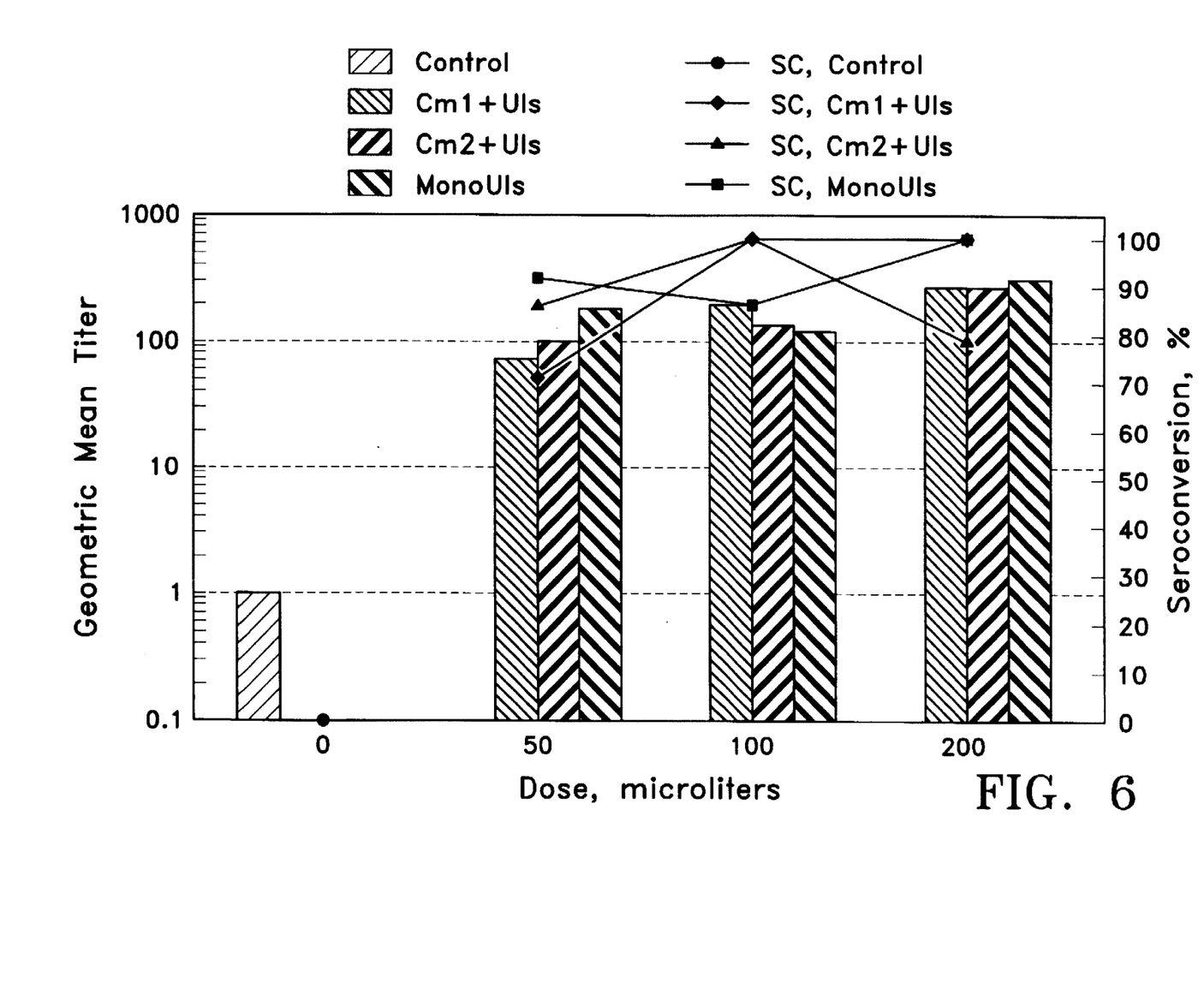
FIG. 6 is a graph showing geometric mean titers and seroconversion white leghorn (WL) chickens vaccinated in ovo at day 18 using an Ulster ND monovalent oil emulsion vaccine and the Ulster vaccine together with one of two experimental inactivated vaccines from a commercial company (Maine Biologics Laboratory) to form two multivalent vaccines.

Viral efficacy at different doses (in microliters) and different antigen concentrations is evaluated based on hemagglutination-inhibition (HI) antibody levels and seroconversion in serum of post-hatch chickens at 3 weeks and 4 weeks of age. HI antibody levels were determined as described in Example 4 above. An HI titer of at least 1:60 is considered to be protective. The results are shown in FIGS. 5 and 6.

For A/turkey/Wisconsin/68 (H5N$_2$) influenza monovalent oil emulsion vaccine, group seroconversion was 85–100% for nonconcentrated antigen, 92–100% for 5× concentrated antigen and 91% for 10× concentrated antigen. Mean hemagglutination-inhibition titers ranged from 1:113 to 1:730 for nonconcentrated antigen, from 1:390 to 1:1194 for 5× concentrated antigen and 1:686 to 1:788 for the 10× concentrated antigen.

For Ulster Newcastle Disease virus monovalent emulsion vaccine, group seroconversion was 86 to 100% for nonconcentrated antigen. Seroconversion was 71% to 100% in the multivalent vaccines when adjusted to antigen levels of a nonconcentrated monovalent vaccine.

The foregoing detailed description is for the purpose of illustration. Such detail is solely for that purpose and those skilled in the art can make variations therein without departing from the spirit and scope of the invention.

INDEX OF THE ELEMENTS DESIGNATED BY A NUMERAL

1. Air Cell
2. Allantoic Cavity
3. Amniotic Cavity
4. Albumin
5. Yolk Sac
6. Embryo
7. Shell Membrane
8. Needle
9. syringe
10. Egg

I claim:

1. A method for immunizing avian embryos comprising puncturing an egg containing said avian embryo with a puncturing means at the longitudinal midline over the egg's air cell in order to administer an oil emulsion vaccine in said egg's albumin end, injecting said vaccine into the egg by vertically inserting a needle means through said air cell to the albumin end, administering said vaccine into the albumin end of the egg, and hatching said egg to obtain an immunized avian species.

2. The method of claim 1 wherein said egg is selected from the group consisting of chicken eggs, turkey eggs, geese eggs, duck eggs, and pheasant eggs.

3. The method of claim 1 wherein said vaccine confers immunity against microbial diseases.

4. The method of claim 1 wherein said vaccine is selected from the group consisting of monovalent and polyvalent vaccines.

5. The method of claim 3 wherein said diseases include Newcastle's disease, avian influenza, avian leukosis, infectious bursal disease, adenovirus disease, reovirus, pox, laryngotracheitis, infectious bronchitis, reticuloendotheliosis, infectious coryza, fowl typhoid, fowl cholera, Salmonella, and Marek's disease.

6. The method of claim 1 wherein said oil emulsion vaccine is a mineral oil emulsion vaccine.

7. The method of claim 1 wherein said needle means is a needle of a gauge selected from the group consisting of 27 gauge, 25 gauge, 23 gauge, 22 gauge, 20 gauge, 18 gauge, and 16 gauge.

8. The method of claim 7 wherein said egg is selected from the group consisting of chicken eggs, turkey eggs, geese eggs, duck eggs, and pheasant eggs.

9. The method of claim 7 wherein said vaccine is an oil emulsion vaccine.

10. The method of claim 7 wherein said vaccine is selected from the group consisting of monovalent and polyvalent vaccines.

11. The method of claim 7 wherein said vaccine confers immunity against microbial diseases.

12. The method of claim 11 wherein said diseases include Newcastle's disease, avian influenza, avian leukosis, infectious bursal disease, adenovirus disease, reovirus, pox, laryngotracheitis, infectious bronchitis, reticuloendotheliosis, infectious coryza, fowl typhoid, fowl cholera, Salmonella, and Marek's disease.

13. The method of claim 9 wherein said oil emulsion vaccine is a mineral oil emulsion vaccine.

14. The method of claim 1 wherein the vaccine is administered at a dose of from about 50 microliters to about 500 microliters.

15. The method of claim 1 wherein the hatchability of the egg is at least about 85%.

16. The method of claim 1 wherein said vaccine is in a concentration of from about 1× to about 10×.

* * * * *